United States Patent [19]
Makrinos et al.

[11] Patent Number: 5,206,894
[45] Date of Patent: Apr. 27, 1993

[54] X-RAY SYSTEM ACCESSORY

[75] Inventors: E. Louis Makrinos, Old Greenwich, Conn.; John Simonton, Arcadia, Okla.

[73] Assignee: Remote Technologies, Inc., a CT Corp., Greenwich, Conn.

[21] Appl. No.: 869,999

[22] Filed: Apr. 16, 1992

[51] Int. Cl.⁵ ............................................. H05G 1/66
[52] U.S. Cl. ..................................... 378/93; 378/114; 378/198
[58] Field of Search ..................... 378/93, 94, 114, 198

[56] References Cited

U.S. PATENT DOCUMENTS 3,790,805  2/1974  Foderaro .
4,170,735  10/1979 Codina .
4,225,787  9/1980  Shapiro .
4,975,937  12/1990 Horton .
5,091,926  2/1992  Horton et al. ...................... 378/114

Primary Examiner—Craig E. Church
Attorney, Agent, or Firm—Blum Kaplan

[57] ABSTRACT

An electromagnetic remote control exposure system including a receiver and transmitter for excitation of a mobile X-ray unit having a rotating anode X-ray tube and exposure mechanism. The transmitter of the remote control is adapted to transmit by a single switch, a first signal to initiate the rotation of the anode and a second signal for the initiation of the actual X-ray exposure. The receiver is provided with a time out delay which causes the X-ray unit to return to the standby mode if the second signal is not received within a predetermined interval of time after receipt of the first signal. The system will also return the X-ray unit to the standby mode if the second signal is interrupted before the exposure has been completed.

6 Claims, 4 Drawing Sheets

X-RAY SYSTEM ACCESSORY

BACKGROUND OF THE INVENTION

This invention relates generally to a remote control system for a mobile X-ray unit and particularly to an electromagnetic exposure switch system for mobile X-ray units that permits rotor preparation and exposure activation of a radiography system.

X-ray units take various forms depending on their intended applications. The vast majority of the units in use today are for medical diagnostic imaging of the human body. These systems are located in hospitals, clinics, and other medical facilities and are usually fixed or stationary installations. These systems are generally installed in lead lined rooms where control of the system takes place from behind a lead lined barrier, thus providing a shielded environment which minimizes the radiation exposure to a facility's X-ray technologists, patients, visitors and other personnel. These systems are also characterized as either having the ability to perform real time imaging which is known as fluoroscopy and/or single exposure filming which is known as radiography. A head-activated fluoroscopic control for the operation of X-ray fluoroscopic units is disclosed in U.S. Pat. No. 4,975,937, dated Dec. 4, 1990, to Horton, et al.

Mobile X-ray units are characterized as movable X-ray systems used to perform radiographic only studies outside of the shielded environment of an X-ray room. These systems are used throughout hospitals in the operating rooms, intensive care units, emergency rooms, or wherever they are needed to perform a study on a patient who cannot be otherwise brought to the X-ray department. U.S. Pat. No. 3,790,805, dated Feb. 5, 1974, to Anthony J. Federaro, describes one type of mobile X-ray unit.

Portable X-ray units are characterized as transportable X-ray systems used to perform radiographic only studies outside of the hospital environment. They tend to be lighter in weight and are easily dismantled which enables the system to be transported in an automobile. These systems are often used to perform radiographic studies in a patient's home. U.S. Pat. No. 4,170,735, dated Oct. 9, 1979, to Codina, et al., describes such a system.

The terms mobile and portable, are often used interchangeably to describe an X-ray system whose primary characteristic is to perform radiographic examinations of patients away from a fixed shielded environment. Operation of X-ray systems of these types require the area to be cleared of all personnel and the technologist to be as far as possible from the equipment during the taking of an X-ray, to minimize potentially harmful radiation exposure.

Whether the X-ray unit is stationary, mobile or portable it will frequently use X-ray tubes whose anode structure is a rotating disc. Specifically, an X-ray tube is a vacuum tube diode type device possessing a cathode structure separated from an anode structure. U.S. Pat. No. 4,225,787, dated Sep. 30, 1980, to Shapiro, et al., explains the operating requirements of an X-ray system employing a rotating anode X-ray tube. Generally speaking, prior to taking an X-ray exposure, the cathode is heated to the required temperature, and the anode is simultaneously "boosted" to the proper rotational speed. A predetermined fixed time interval is allowed for the cathode to heat and for the anode disc to accelerate. When the fixed time interval has elapsed, and when the system receives the exposure command, high voltage is then applied between the anode and the cathode which will subsequently cause the tube to generate X-rays.

The above described X-ray units possess electrical circuits activated by an exposure switch to control the necessary X-ray tube functions needed to make a radiographic exposure. Specifically, X-ray machines which employ a rotating anode X-ray tube have an exposure switch which is comprised of a double set of electromechanical switches. The first electrochemical switch includes a set of contacts coupled to the rotor circuitry to affect the rotation of the anode and the heating of the cathode. Once the anode reaches the desired speed and the cathode is heated, a second electromechanical switch includes a set of contacts coupled to the exposure circuitry so that activation of the second set of contacts will initiate a radiographic exposure with no further delay.

Exposure switches for X-ray units can take various forms. Although their configurations may vary, the exposure switches of mobile and portable X-ray units are connected to the unit by an electrical cable of limited length. U.S. Pat. No. 4,170,735, dated Oct. 9, 1979, to Codina, et al., discloses a portable X-ray unit having a hand held remote control mechanically and electrically connected to the X-ray unit by a cable. A remote control exposure switch connected by a cable of a limited length suffers many disadvantages as the X-ray technologist endeavors to get as far away as possible from the machine during the actual taking of an X-ray exposure. The lack of an X-ray shielded environment during the taking of a mobile or portable X-ray exposure necessitates this procedure to minimize the harmful effects of accumulated doses of ionizing radiation received by the X-ray technologist.

Many potentially unsafe incidents can occur when conventional exposure switch cords are extended. For example, when extended, the exposure switch cord can topple an intravenous pole, dislodge a catheter, interfere with monitoring electrodes, respirators, or other forms of life support equipment.

Another disadvantage is that, when extended, these cables are subjected to mechanical stress. Mechanical stress to the interconnecting electrical cable often results in this cable being cut or frayed which can result in shorted or open electrical connections. Cut cables can present a shock safety problem while a shorted cable can cause serious damage to the rotating anode X-ray tube. Yet another disadvantage of previous X-ray exposure switches is they require the continuous activation of a plurality of electrical switches to prepare the rotating anode X-ray tube and create a radiographic exposure. The problem with these types of switches is that the multiple electromechanical switch mechanisms often jam. Jammed switch mechanisms which go undetected can cause excessive heat to build up in the X-ray tube and create a severe safety problem. Still another disadvantage of faulty electrically connected X-ray exposure switches is that they can cause incomplete exposures which necessitate retakes or unwarranted exposures, which expose both the technologist and patient to unnecessary potentially harmful radiation. Accordingly, an electromagnetic remote control exposure switch system for a mobile X-ray unit which is safe to use from a patient perspective and from a technologist perspective and that overcomes the disadvantages noted above, is desired.

SUMMARY OF THE INVENTION

Generally speaking, in accordance with the invention, an electromagnetic remote control exposure switch system for use with a mobile X-ray unit, is provided. The exposure switch system is composed of a hand held, single switch infrared transmitter and a receiver which is hardwired to the X-ray unit. The infrared remote control exposure switch system is constructed and arranged to direct infrared signals in two consecutive successive detection cycles for exposure switch activation. Upon detection of the first infrared signal the system issues the boost command to the X-ray machine which starts the rotation of the anode. In response to the second detection cycle of the infrared signal, within a predetermined period of time, the system issues the exposure command and an X-ray exposure takes place. If the second activation does not occur within the predetermined period of time, the system will automatically return the X-ray unit to the standby mode. The second detection cycle must take place for the entire length of the exposure, otherwise, upon release of the switch, the system will return the X-ray machine to standby, interrupting the exposure in progress. The length of the exposure is predetermined when the technologist sets the exposure length on the X-ray unit itself. If the transmitter switch is activated for the second time, for a time period which exceeds the exposure length, the exposure will terminate according to the original setting on the X-ray unit itself. Release of the second switch activation restores the X-ray machine to the standby mode.

Accordingly, it is an object of this invention to provide an electromagnetic remote control exposure switch system for use with a mobile X-ray unit that increases technologist and patient safety when performing a mobile X-ray diagnostic procedure.

Another object of the invention is to provide an electromagnetic remote control exposure switch system which allows rotor preparation and exposure activation of a mobile X-ray unit from a considerable distance at a plurality of angles.

A further object of the invention is to provide an electromagnetic remote control exposure switch system for activating a mobile X-ray unit which substantially eliminates false triggering of the X-ray unit.

Yet another object of the invention is to provide an electromagnetic remote control exposure switch system with increased reliability because it is subjected to fewer mechanical stresses of the type that cause equipment failure and down time.

Yet a further object of the invention is to provide an electromagnetic remote control exposure switch system for a mobile X-ray unit which will minimize X-ray tube burn-out.

Still other objects and advantages of the invention will in part be obvious and will in part be apparent from the specification.

The invention accordingly comprises the features of construction, combination of elements, and arrangement of parts which will be exemplified in the construction hereinafter set forth, and the scope of the invention will be indicated in the claims.

BRIEF DESCRIPTION OF THE DRAWINGS

For a fuller understanding of the invention, reference is had to the following description taken in connection with the accompanying drawings, in which.

DETAILED DESCRIPTION OF THE PREFERRED EMBODIMENTS

Figure 1:
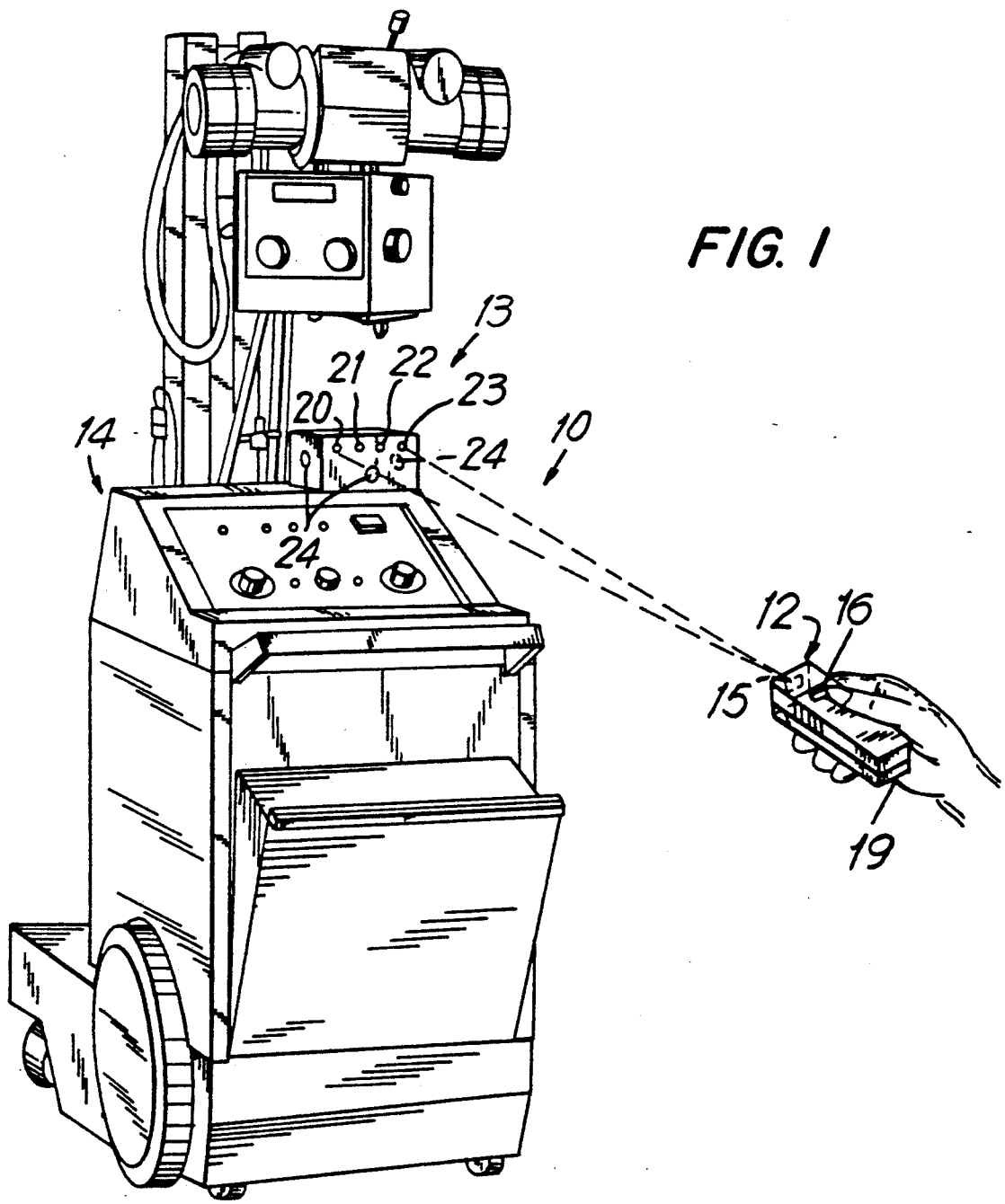
FIG. 1 is a perspective view of an electromagnetic remote control exposure switch system for a mobile X-ray unit constructed in accordance with a preferred embodiment of the instant invention.

Reference is first made to FIG. 1 wherein an infrared remote control exposure switch system for a mobile X-ray unit, generally indicated at 10, is depicted. The system includes an infrared transmitter, generally indicated as 12, which activates an infrared receiver, generally indicated as 13, which is electrically and mechanically coupled to a mobile X-ray unit, generally indicated as 14. Infrared receiver 13 includes four LED's 20, 21, 22, and 23 and three infrared detectors 24.

Figure 2:
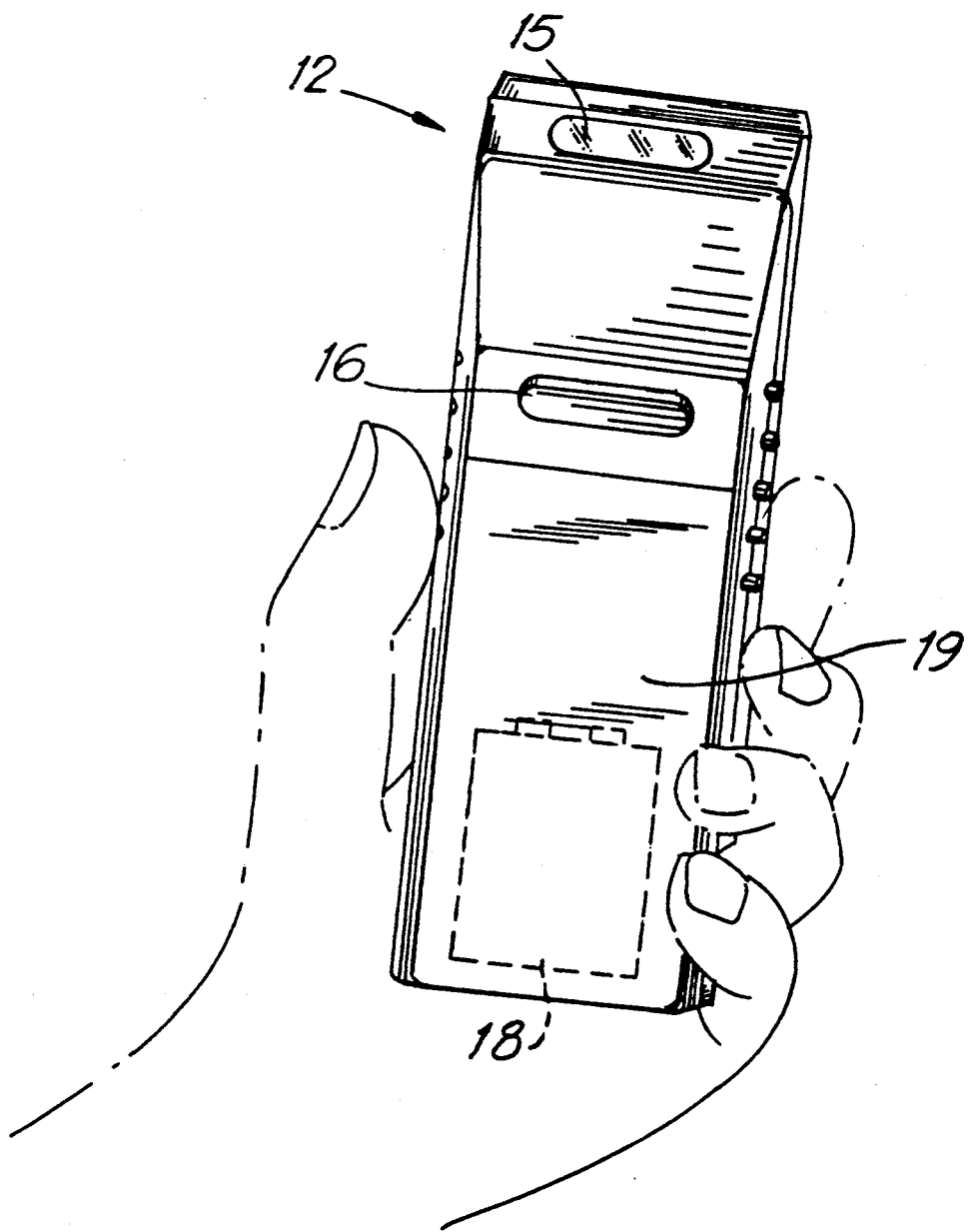
FIG. 2 is a top plan view of the transmitter constructed in accordance with a preferred embodiment of the instant invention.
Figure 3:
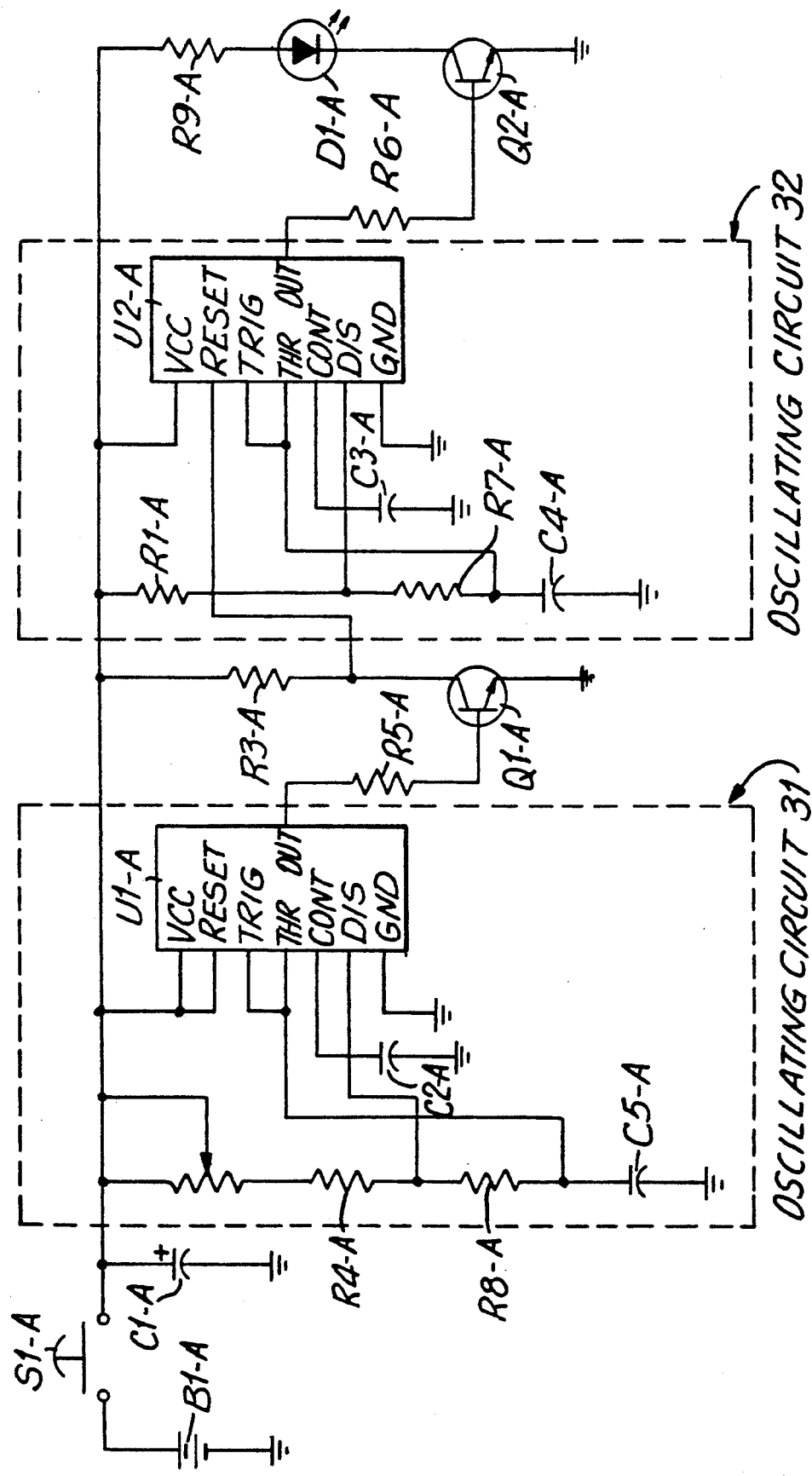
FIG. 3 is a detailed circuit diagram of the transmitter constructed in accordance with a preferred embodiment of the instant invention.

Referring next to FIG. 2, the transmitter 12 includes a housing 19 for supporting therein certain electronic circuitry, which are more particularly illustrated in FIG. 3, and further supports an infrared diode 15 and a push button 16. The transmitter is powered by battery 18.

Transmitter 12 is operated by actuation of push button 16. In an exemplary embodiment, actuation of push button 16 activates infrared diode 15, which produces a 38 kHz carrier beam of infrared radiation with a wavelength of 940 nm pulsed modulated at 200 Hz. LED 20 on receiver 13 will indicate when power to the receiver has been applied. Upon the first actuation of push button 16, if transmitter 12 is within 24 feet of receiver 13 and directed horizontally towards one of the three infrared detectors 24 on receiver 13, LED's 21, and 22 are activated. LED 21 indicates that the infrared signal has been received. LED 22 indicates that the rotor has been excited which also occurs after the first actuation of push button 16.

A second actuation of push button 16 again activates infrared diode 15 with the same 940 nm infra-red signal being sent by the same carrier and at the same modulation. This activation will cause an exposure to take place, LED 22 remains on and LED 23 turns on and indicates that the exposure command is in effect. If push button 16 is not actuated within fifteen (15) seconds of the first actuation, the system will automatically cause the rotor to be deactivated and LED 21 and 22 to turn off.

Reference is next made to FIG. 3 where transmitter circuitry for actuating the operation described above, generally indicated as 30, is depicted. Battery B1-A is connected through a switch S1 and then first to capacitor C1-A which stores power during the portion of the 200 Hz modulating frequency when infrared emitter D1-A is off and also lowers the effective internal impedance of the battery to allow maximum radiated power.

Switch S1-A is also connected to an oscillating circuit, generally indicated as 31, having a variable resistor R2-A, resistors R4-A and R8-A, capacitors C2-A and C5-A and U1-A which is a 555 timer. In a preferred embodiment battery B1-A has a value of 9 volts, capacitor C1-A is an electrolytic capacitor which has a value of 100 $\mu$Fd, variable resistor R2-A has a value of 100 kohms, resistor R4-A has a value of 33 kohms, resistor R8-8 has a value of 330 kohms, capacitor C5-A is a Mylar capacitor which has a value of 0.01 $\mu$Fd and capacitor C2-A is a ceramic disk capacitor which has a value of 0.01 $\mu$Fd. U1-8 is wired as an oscillator with the values of resistors R2-A, R4-A and R8-A and capacitors C2-A and C5-A chosen to produce a 200 Hz rectangular pulse output with a duty factor of 30 percent. The output of oscillating circuit 30 is connected to resistor R5-A which in turn is connected to transistor Q1-A. In a preferred embodiment resistor R5-A has a value of 2.2 kohms. The collector of transistor Q1-A is connected to both a pull up resistor R3-A and the reset pin of another 555 timer U2-A which is wired to form oscillating circuit 32. The output of oscillating circuit 31 modulates oscillating circuit 32 by turning U2-A on and off by way of transistor Q1-A which alternately grounds the reset pin of U2-A. This turns oscillator 32 off which allows oscillator 32 to free run. Resistors R7-A and R1-A and capacitors C3-A and C4-A are selected to produce a 38 kHz rectangular pulse at the output of U2-A with a duty cycle of 30 percent. Resistors R1-A and R7-A are 10 kohms, resistor R3-A is 22 kohms, resistor R5-A is 2.2 kohms, capacitor C4-A is a ceramic disk capacitor of 0.001 $\mu$Fd and capacitor C3-A is a ceramic disk capacitor having a value of 0.01 $\mu$Fd. The output of U2-A is connected to resistor R6-A which in turn is connected to the base of transistor Q2-A which drives the infrared diode D1-A when transistor Q2-A is turned on. Resistor R6-A has a preferred value of 2.2 kohms and resistor R9-A has a preferred value of 100 ohms.

Figure 4:
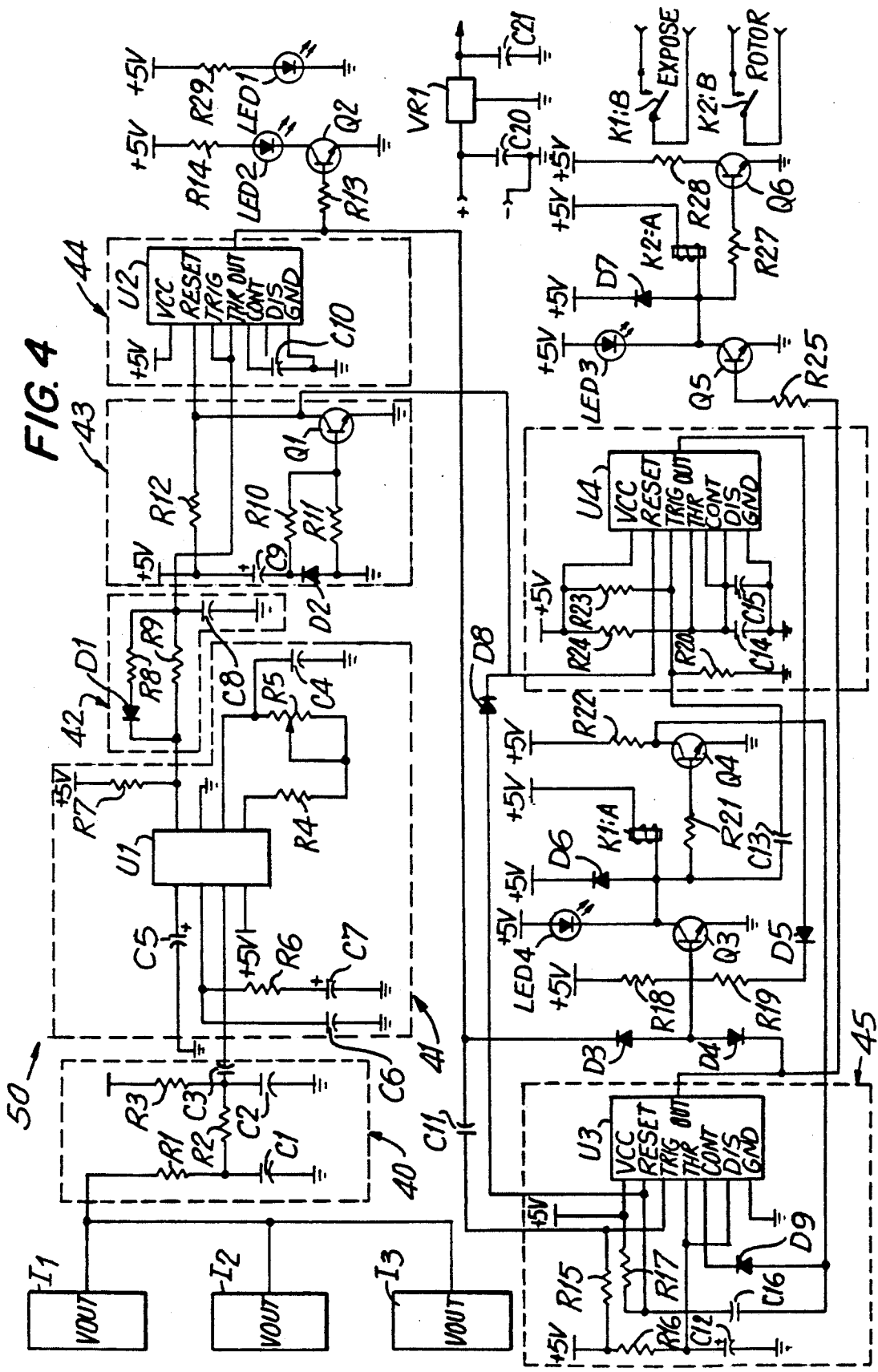
FIG. 4 is a detailed circuit schematic of the receiver constructed in accordance with a preferred embodiment of the instant invention.

Reference is now made to FIG. 4 where the electric circuitry of the receiver is indicated generally as 50. Power is supplied to the receiver through the mobile X-ray unit. The DC voltage passes through a voltage regulator VR1 which provides a regulated voltage of 5 volts. Light emitting diode LED1 is connected through pull up resistor R29 to power. When power is supplied to the receiver LED1 will light. Resistor R29 has a value of 220 ohms, capacitor C20 has a value of 33 $\mu$Fd, and capacitor C21 has a value of 1000 $\mu$Fd. The three infrared detectors I1, I2 and I3 are mounted inside the receiver at 90 degree angles in the horizontal plane to allow the receiver a 325 degree field of view. These three detectors detect infrared radiation with a wavelength of 940 nm and check for the presence of the 38 kHz carrier frequency. The carrier frequency bandwidth of these detectors run from approximately 20 kHz to 60 kHz at the half power points. In response to the 200 Hz modulated infrared carrier beam the detector modules output a signal which consists of only the modulation frequency. The outputs of all the detector modules I1, I2 and I3 are connected to low pass filter 40 for attenuation. In a preferred embodiment resistors R1 and R2 have a value of 10 kohms, resistor R3 has a value of 1 Mohms, and capacitors C1, C2 and C3 are 0.05 $\mu$Fd ceramic disk capacitors. The output of low pass filter 40 is connected to tone decoder 41. Resistors R4, R5 and capacitor C4 set the center frequency of the tone decoder 41 at 200 Hz. In a preferred embodiment resistor R4 has a value of 15 kohms, resistor R5 is a 50 kohm trimmer potentiometer and capacitor C4 is a 0.1 $\mu$Fd Mylar capacitor. The acquisition time of the decoder, which is the amount of time the signal must be present before it is recognized, is set by the values of resistor R6 and capacitors C6 and C7. In a preferred embodiment resistor R6 is 4.7 kohms, capacitor C6 is an electrolytic capacitor of 4.7 $\mu$Fd, capacitor C7 is an electrolytic capacitor of 1 $\mu$Fd and capacitor C5 is an the tone decoder 41 is connected to delay network 42 consisting of resistors R8 and R9, capacitor C8, and diode D1 which in turn serves to trigger U2, which is wired to serve simply as a threshold detector with hysteresis. Resistor R7 is a pull up resistor having a preferred value of 4.7 kohms, resistor R8 has a preferred value of 150 kohms, resistor R9 of 1 Kohm and capacitor C8 which is a Mylar capacitor having a value of 0.1 $\mu$Fd.

The output of the delay network 42 is used to trigger the threshold detector 44. The threshold detector 44 includes a 555 timer U2 wired to serve as a threshold detector with hysterises. Connected to the reset pin of U2 is a cold start circuit 43. In a preferred embodiment resistors R10 and R12 are 22 kohms, resistor R11 is 330 kohms, capacitor C10 is a 0.01 $\mu$Fd ceramic disk capacitor, and capacitor C9 is a 4.7 $\mu$Fd electrolytic capacitor.

The output of the threshold detector 44 is connected through resistor R13 to transistor Q2 which is used to drive the "receive" indicator LED2 which has its cathode connected to the collector of transistor Q2 and its anode connected to a pull up resistor R14. In an exemplary embodiment resistor R13 is 2.2 kohms and resistor R14 is 220 ohms. The output of the threshold detector 44 is also coupled by capacitor C11 to the monostable circuit 45. The monostable circuit 45 is triggered on the falling edge of the output of the threshold detector 44. This provides the fifteen second timeout period in which a second signal must be received or the rotor will disarm. In a preferred embodiment resistor R15 is 1 Mohm, resistor R16 is 1.5 Mohm, resistor R17 is 22 kohms, capacitor C12 is an electrolytic capacitor of 10 $\mu$Fd and capacitor C16 is an electrolytic capacitor having a value of 10 $\mu$Fd.

The output of the monostable circuit 45 is connected through resistor R25 to the base of transistor Q5 which, in turn, activates the rotor driver relay K2:A and light emitting diode LED3 which is the "rotor on" indicator. Resistors R25 and R27 are 2.2 kohm resistors and resistor R28 is a 91 ohm resistor. Transistor Q6 is arranged to be on during the time Q5 is off and vice-versa. This provides equalization of current drain into the receiver circuit, making the job of voltage dropping from a high voltage supply, and voltage regulation to the receiver circuitry easier. The output of the monostable circuit 45 is also logically ANDED to the output of the threshold detector 44 by diodes D3 and D4 and, in turn, activates transistor Q3 which is the driver for relay K1:A which activates the exposure mechanism in the mobile X-ray unit. Relays K1:A and K2:A are hard wired to the exposure switch and rotor switch respectively and the mobile X-ray unit. Transistor Q3 is also the driver for light emitting diode LED4 which indicates an exposure is taking place. This logical combination will only allow relay K1:A to close during the time that a signal is being received and as long as a delay between two signals has not been more than fifteen (15) seconds. Resistor 19 has a value of 270 ohms and resistor R18 has a value of 10 kohms, resistor R21 has a value of 2.2 kohms and resistor R22 has a value of 91 ohms. When transistor Q3 is activated, the voltage change at its collector terminal is coupled by capacitor C13 to another 555 timer U4, which is wired as another monostable circuit 46. When a negative outgoing pulse is received at the input of monostable circuit 46, it switches to its activated state for a period of approximately one half of a second and over-rides the ANDED combination of the threshold detector 44 and monostable circuit 45. This action will hold the receiver in its mode for making an exposure for a period of time on the order of a half of a second even if the infrared beam is interrupted.

In the case of a long exposure, the output of transistor Q4 is coupled by diode D9 to monostable circuit 45 so that if a long exposure signal is received, it will over-ride the fifteen second time out. Also, because of capacitor C16, the monostable circuit 45 is reset when the transmitter signal is terminated. Resistor R20 has a value of 1 Mohm, resistor R24 has a value of 420 khoms resistor R23 has a value of 330 kohms, capacitor C14 is a 1 µFd electrolytic capacitor and capacitor C15 is a 0.01 µFd ceramic disk capacitor. The reset pin of U3 is coupled by diode D8 to the reset pin of U4.

It will thus be seen that the objects set forth above, among those made apparent from the preceding description, are efficiently attained and, since certain changes may be made in the above construction without departing from the spirit and scope of the invention, it is intended that all matter contained in the above description or shown in the accompanying drawings shall be interpreted as illustrative and not in a limiting sense.

It is also to be understood that the following claims are intended to cover all of the generic and specific features of the invention herein described and all statements of the scope of the invention which, as a matter of language, might be said to fall therebetween.

What is claimed is:

1. An electromagnetic remote control system adapted to transmit an electromagnetic signal for exposure of a mobile X-ray unit having a rotor preparation means and exposure initiate means for producing a radiographic exposure comprising in combination: transmitter means including a manually operated switch means for selectively transmitting a first electromagnetic signal and a second electromagnetic signal and receiver means adapted to be selectively electrically coupled to the mobile X-ray unit and adapted for receiving said first and second electromagnetic signals and in response to said first electromagnetic signal said receiving means is required to effect rotation of said rotor preparation means, and in response to said second electromagnetic signal said receiving means is required to effect excitation of said exposure initiate means to produce a radiographic exposure, said receiver means including deactivation means for deactivating the rotor means when said second electromagnetic signal is delayed beyond a predetermined time interval after said first electromagnetic signal, said deactivation means being further adapted to deactivate the exposure initiate means when said second electromagnetic signal is interrupted.

2. The remote control of claim 1, wherein said transmitting means transmits an infrared signal.

3. The remote control of claim 1, wherein said transmitting means emits a beam of infrared radiation with a predetermined wavelength which is modulated by two distinct frequency signals; and receiver means adapted to receive first said infrared beam and electrically excite said rotor means and receive said second infrared beam and electrically excite said exposure means.

4. The remote control of claim 1, wherein said transmitting means emits a continuous pulsed beam which is modulated by both 200 Hz and 38 kHz signals.

5. The remote control of claim 1, wherein said receiver means includes detector means which are adapted to detect signals at a plurality of angles.

6. The remote control of claim 1, wherein said detector means are oriented to receive only horizontally directed signals.

* * * * *